United States Patent [19]

Shay et al.

[11] 4,439,525

[45] Mar. 27, 1984

[54] **HIGH METHIONINE CONTENT *PICHIA PASTORIS* YEASTS**

[75] Inventors: Lucas K. Shay; Eugene H. Wegner, both of Bartlesville, Okla.

[73] Assignee: Phillips Petroleum Company, Bartlesville, Okla.

[21] Appl. No.: 300,521

[22] Filed: Sep. 9, 1981

[51] Int. Cl.$^3$ .................. C12N 1/32; C12N 1/16; C12R 1/84

[52] U.S. Cl. .................. 435/247; 435/172; 435/255; 435/804; 435/938; 426/60; 426/62; 426/656

[58] Field of Search .................. 435/68, 113, 172, 255, 435/804, 247, 813, 938; 426/656, 62, 60

[56] References Cited

U.S. PATENT DOCUMENTS

| | | | |
|---|---|---|---|
| 3,219,543 | 11/1965 | Douros, Jr. et al. | 195/1 |
| 3,391,061 | 7/1968 | McNeely | 195/31 |
| 3,687,816 | 8/1972 | Marraro | 195/100 |
| 3,713,976 | 1/1973 | Bunting et al. | 195/28 R |
| 3,713,984 | 1/1973 | Bunting et al. | 195/82 |
| 3,730,837 | 5/1973 | Iguchi et al. | 435/247 |
| 3,855,063 | 12/1974 | Nagasawa et al. | 435/68 |
| 3,966,553 | 6/1976 | Charpentier et al. | 435/144 |
| 3,981,774 | 9/1976 | Hitzman | 435/247 |
| 4,168,201 | 9/1979 | Wegner | 435/247 |
| 4,218,538 | 8/1980 | Church | 435/101 |
| 4,226,939 | 10/1980 | Wegner | 435/255 |

FOREIGN PATENT DOCUMENTS

| | | | |
|---|---|---|---|
| A0017853 | 10/1980 | European Pat. Off. | 435/255 |
| 2006235 | 12/1969 | France | 435/247 |

OTHER PUBLICATIONS

Okanishi et al., "Isolation of Mutants of *Canadida tropicalis* with Increased Methionine Content", Canadian Journal of Microbiology, 16(12), (1970), pp. 1139–1143.

Wiken et al., "Growth of the Methanol Assimilating Yeast *Pichia pastoris* Phaff in Batch Culture", Alkoholi Teollisuus Tutkimus, (1977), pp. 220–226, Chemical Abstracts 91:54563h.

Wegner, "Single Cell Protein Material and Pure Culture", European Patent Application 17,853.

*Chem. Abst:* 94, (1981), 28898p.

Vary, "Spore Germination of *Baccillis megaterium* QMB1551, Mutants", *Journal of Bacteriology*, Oct. 1972, pp. 640–642.

Schlessinger (Editor), *Microbiology*–1976, Am. Society for Microbiology, (Wash. D.C., 1976), pp. 507–527 (article by Von Vorstel et al., "Mutation and Selection Systems for Yeast").

Miller, *Experiments in Molecular Genetics*, (Cold Spring Harbor Laboratory, 1971), pp. 113–139.

Reviere, *Industrial Applications of Microbiology*, (John Wiley, 1977), pp. 105–149.

*Primary Examiner*—Thomas G. Wiseman
*Assistant Examiner*—John E. Tarcza

[57] ABSTRACT

Mutant yeasts of the strain *Pichia pastoris* have been developed which contain relatively high levels of methionine. These high methionine content *Pichia pastoris* mutants grow on an oxygenated hydrocarbon such as methanol, to produce improved amino acid balance single-cell protein product eliminating or reducing the need to supplement single-cell protein with methionine when used as food supplements.

37 Claims, No Drawings

HIGH METHIONINE CONTENT *PICHIA PASTORIS* YEASTS

FIELD OF INVENTION

The invention pertains in one aspect to novel strains of *Pichia pastoris* yeasts. In another aspect, the invention pertains to *Pichia pastoris* yeast strains with increased methionine content. In a further aspect, the invention pertains to methods of producing, and the products resulting from producing, single cell protein on oxygenated hydrocarbon substrates utilizing the increased methionine type improved yeasts.

BACKGROUND OF THE INVENTION

In the decade of the 1950s, predictions were made of an impending global protein shortage. Interest developed in the potential of microbiologically-produced protein as an animal feed supplement, and, possibly, as a human dietary constituent.

Yeasts are known for a high nutritional value, and have been used for a long time as feed supplements, both for animals, and to some extent for humans. Yeasts have a high protein content in general, and probably contain more B-group vitamins than most other protein sources, $B_{12}$ a notable exception. However, yeasts are also known to be low in some of the sulfur-containing amino acids, particularly methionine.

TABLE I[a]

ESSENTIAL AMINO ACIDS OF SOME PROTEIN SOURCES[b]

|  | Wheat | Egg White | Saccharomyces Cerevisiae | Candida Lypolytica | Pichia pastoris NRRL Y-11430[c] |
|---|---|---|---|---|---|
| Lysine | 2.8 | 6.5 | 7.7 | 7.8 | 6.1 |
| Threonine | 2.9 | 5.1 | 4.8 | 5.4 | 5.6 |
| Methionine | 1.5 | 3.2 | 1.7 | 1.6 | 1.2 |
| Cystine | 2.5 | 2.4 | — | 0.9 | 0.7 |
| Tryptophan | 1.1 | 1.6 | 1.0 | 1.3 | 0.7 |
| Isoleucine | 3.3 | 6.7 | 4.6 | 5.3 | 5.5 |
| Leucine | 6.7 | 8.9 | 7.0 | 7.8 | 7.8 |
| Valine | 4.4 | 7.3 | 5.3 | 5.8 | 6.5 |
| Phenylalanine | 4.5 | 5.8 | 4.1 | 4.8 | 4.1 |

[a]Data from p. 110 Industrial Applications of Microbiology, J. Riviere, (Wiley 1977).
[b]The values shown are g amino acid/100 g protein.
[c]Methionine content in *Pichia pastoris* Y-11430 is 1.2 g/100 g protein (as shown) which equals 0.8 g/100 g weight.

TABLE II[a]

LIMITING AMINO ACIDS OF COMMON FOOD PROTEIN

| Food Source | Limiting Amino Acids | % Deficiency[b] |
|---|---|---|
| Whole Egg | none | 0 |
| Beef | Cystine and Methionine | 29 |
| Cow's Milk | Cystine and Methionine | 32 |
| Rice, Wheat, Maize | Lysine | 61–72 |
| Baker's Yeast | Cystine and Methionine | 55 |

[a]p. 112 of reference cited Table I footnote a.
[b]Compared with whole egg.

As can be seen above, added methionine is needed when yeasts are to be used as animal feeds.

Needed are suitable yeasts that have good productivity in single cell protein production, but with much increased (enhanced) methionine content.

BRIEF DESCRIPTION OF THE INVENTION

We have discovered mutant yeasts of *Pichia pastoris* which strains contain much increased amounts of methionine, up to such as about 3.5 weight percent. Further, we have employed these mutant high-methionine strains in processes for the production of single cell protein. The so-produced single cell protein product utilizing these mutant yeasts has much improved methionine content to the extent that supplementation for feed use purposes with added methionine is greatly reduced or indeed even eliminated.

Our discovery includes in its several aspects 36 new and novel *Pichia pastoris* mutant yeast strains of much increased methionine content, which strains have been deposited in due course prior to the filing of this application with the U.S. Dept. of Agriculture, Northern Regional Research Laboratory, and which strains have received individual depository numbers as hereinafter disclosed.

DETAILED DESCRIPTION OF THE INVENTION

It is theorized that over eons of evolution, microorganisms have been developing better and tighter regulatory mechanisms so that they tend not to overproduce unnecessary metabolites. In order to survive, all microorganisms must possess controls over the biosynthesis of cellular components such as amino acids. It is believed that two primary mechanisms exist for the biosynthesis of amino acids by microorganisms: (1) the allosteric inhibition of enzyme activity through feedback inhibition of the first reaction in this productive sequence by the end product of the reactions; and (2) coarse control which may be described as the genetic repression or derepression of enzyme synthesis. It seems likely that the biosynthesis of methionine in yeast is governed by both mechanisms.

Since we considered it impossible to increase biosynthetic enzyme activity unless the resulting methionine was excreted from yeast cells, and since the biosynthesis of methionine is tightly controlled by the cells, it appeared that addition or insertion of extra copies of genes coded for the biosynthetic enzymes would not produce much if any in the way of methionine increase. Thus, our attention turned to means to desynthesize or to bypass the control mechanisms so that the synthesis of methionine would be resistant to feedback inhibition or feedback repression.

We developed methods, to interfere in the otherwise tightly controlled regulatory mechanisms of the cells, and thus we have produced mutant strains of *Pichia pastoris* which overproduce methionine. The method we employed for strain improvement is desensitization of the regulatory mechanism governing methionine synthesis by the aid of analogs. These analogs are termed toxic analogs or antimetabolites of methionine.

To the best of our knowledge, no *Pichia pastoris*-derived strains of increased methionine content have ever, heretofore, been developed or produced. Nor, to the best of our knowledge, have heretofore been produced single-cell proteins from *Pichia pastoris* strains of such high methionine contents from strains growing on oxygenated hydrocarbon feedstocks.

Improved methionine containing *Pichia Pastoris* strains

Base Strain

The *Pichia pastoris* strains of improved methionine content which we have developed are derived from *Pichia pastoris* NRRL Y-11430. This *Pichia pastoris* NRRL Y-11430 itself has highly desirable and useful properties, growing particularly well at higher mineral salts levels and hence higher yeast cell densities in a ferment, and showing high productivity on oxygenated hydrocarbon feedstocks, particularly lower alcohols most preferably methanol.

The designation NRRL Y-11430 reflects the fact that this parent strain itself was deposited with the official depository at the U.S. Dept. of Agriculture, Agricultural Research Service, Northern Regional Research Laboratory, Peoria, Ill. 61604. By depositing therewith appropriate cultures, we have received from the depository the individual designation NRRL Y-11430 as indicated. This culture was deposited in accordance with the procedure of the Department of Agriculture such that the progeny of the strain will be available during pendency of this patent application to one determined by the Commissioner of Patents and Trademarks to be entitled thereto according to the rules of practice and patent cases and according to 35 U.S.C. 122. The aforesaid deposit was made in accordance with Patent and Trademark Office practices and rules such that all restrictions on availability to the public of progeny of NRRL Y-11430 is to be removed upon granting of a patent of which said strain is the subject, so that said strain will be available to provide samples for utilization in accordance with the disclosure thereof upon issuance of the patent describing the same in the United States.

In accordance with one aspect of our invention, we derived from treatment of this *Pichia pastoris* NRRL Y-11430 and developed 36 mutant strains which exhibit highly enhanced methionine producing capabilities.

These 36 mutant *Pichia pastoris* strains are each unique, novel, and each also has been deposited with the aforesaid depository. These unique cultures grow particularly well at higher mineral salts levels, producing high cellular densities in fermentation procedures on oxygenated hydrocarbons employing aerobic fermentation conditions, and exhibit high productivity on oxygenated hydrocarbon feedstocks, particularly lower alcohols such as methanol. These unique species which we have developed are designated as follows:

| Culture Name | Our Strain Designation | Depository Designation |
| --- | --- | --- |
| Pichia pastoris | E4 | NRRL Y-12437 |
| Pichia pastoris | E6-12 | NRRL Y-12438 |
| Pichia pastoris | E6-15 | NRRL Y-12439 |
| Pichia pastoris | E6-18 | NRRL Y-12440 |
| Pichia pastoris | E8-5 | NRRL Y-12441 |
| Pichia pastoris | E8-17 | NRRL Y-12442 |
| Pichia pastoris | E8-31 | NRRL Y-12443 |
| Pichia pastoris | E8-43 | NRRL Y-12444 |
| Pichia pastoris | E8-50 | NRRL Y-12445 |

-continued

| Culture Name | Our Strain Designation | Depository Designation |
| --- | --- | --- |
| Pichia pastoris | E8-52 | NRRL Y-12446 |
| Pichia pastoris | E8-60 | NRRL Y-12447 |
| Pichia pastoris | E8-64 | NRRL Y-12448 |
| Pichia pastoris | E8-64-12 | NRRL Y-12449 |
| Pichia pastoris | E8-64-45 | NRRL Y-12450 |
| Pichia pastoris | E8-64-48 | NRRL Y-12451 |
| Pichia pastoris | E10-7 | NRRL Y-12452 |
| Pichia pastoris | E10-9 | NRRL Y-12453 |
| Pichia pastoris | E10-10 | NRRL Y-12454 |
| Pichia pastoris | E10-17 | NRRL Y-12455 |
| Pichia pastoris | E10-19 | NRRL Y-12456 |
| Pichia pastoris | E6-20 | NRRL Y-12457 |
| Pichia pastoris | E6-22 | NRRL Y-12458 |
| Pichia pastoris | E2-1 | NRRL Y-12459 |
| Pichia pastoris | E8-10 | NRRL Y-12460 |
| Pichia pastoris | E8-34 | NRRL Y-12461 |
| Pichia pastoris | E8-62 | NRRL Y-12462 |
| Pichia pastoris | E8-64-22 | NRRL Y-12463 |
| Pichia pastoris | E10-3 | NRRL Y-12464 |
| Pichia pastoris | E10-5 | NRRL Y-12465 |
| Pichia pastoris | E10-6 | NRRL Y-12466 |
| Pichia pastoris | E10-8 | NRRL Y-12467 |
| Pichia pastoris | E10-15 | NRRL Y-12468 |
| Pichia pastoris | E10-12 | NRRL Y-12469 |
| Pichia pastoris | E10-11 | NRRL Y-12470 |
| Pichia pastoris | E10-14 | NRRL Y-12471 |
| Pichia pastoris | E8-64-94 | NRRL Y-12493 |

Each of the aforesaid NRRL designations reflects the fact that we have deposited each of these 36 novel yeast cultures with the official depository, by depositing therein two agar slant cultures of each, and have received from the aforesaid depository the individual strain designations as indicated. These unique cultures have been deposited in accordance with the procedures of the depository, and of the U.S. Patent and Trademark Office, such that the progeny of these strains will be available during pendency of this patent application to one determined by the Commissioner of Patents and Trademarks to be entitled thereto, as required by rules of practice in patent cases and 35 U.S.C. 122. These deposits are made in accordance with Patent and Trademark Office practice such that all restrictions on availability to the public of the progeny of these strains will be irrevocably removed upon granting of a United States Patent of which these important strains are the subject, so that these strains thereupon become available to provide samples for utilization in accordance with our invention. Culture samples from these deposits, or from our cultures from which the deposits were made, thus provide ready availability of samples of strains of our discovery.

Our invention provides, in one aspect, in processes for culturing oxygenated hydrocarbon-assimilating microbial cells belonging to these 36 new cultures (strains) microorganisms under aqueous aerobic culturing conditions. These novel and unique microorganisms derived from *Pichia pastoris* have each been classified as follows:
Division: Ascomytina
Class: Hemiascomycetes
Order: Endomycetales
Family: Saccharomycetaceae
Genus: Pichia The novel and unique strains of microorganisms can be further characterized by properties as shown in the following tabulation.

| Mutant Isolate | Gram Staining | Sporulation | Growth Factor | Colony Appearance | Colony Color On IM2-M plate | YM | PC | Nutrient Agar | IM2-Glucose | IM2-Methanol | IM2-Ethanol | IM2-Formaldehyde |
|---|---|---|---|---|---|---|---|---|---|---|---|---|
| E4 | + | + | biotin | circular raised | white | + | + | + | + | + | + | − |
| E6-12 | + | + | " | " | " | + | + | + | + | + | + | − |
| E6-15 | + | + | " | " | " | + | + | + | + | + | + | − |
| E6-18 | + | + | " | " | " | + | + | + | + | + | + | − |
| E8-5 | + | + | " | " | " | + | + | + | + | + | + | − |
| E8-17 | + | + | " | " | " | + | + | + | + | + | + | − |
| E8-31 | + | + | " | " | " | + | + | + | + | + | + | − |
| E8-43 | + | + | " | " | " | + | + | + | + | + | + | − |
| E8-50 | + | + | " | " | " | + | + | + | + | + | + | − |
| E8-52 | + | + | " | " | " | + | + | + | + | + | + | − |
| E8-60 | + | + | " | " | " | + | + | + | + | + | + | − |
| E8-64 | + | + | " | " | " | + | + | + | + | + | + | − |
| E8-64-12 | + | + | " | " | " | + | + | + | + | + | + | − |
| E8-64-45 | + | + | " | " | " | + | + | + | + | + | + | − |
| E8-64-48 | + | + | " | " | " | + | + | + | + | + | + | − |
| E8-64-94 | + | + | " | " | " | + | + | + | + | + | + | − |
| E10-7 | + | + | " | " | " | + | + | + | + | + | + | − |
| E10-9 | + | + | " | " | " | + | + | + | + | + | + | − |
| E10-10 | + | + | " | " | " | + | + | + | + | + | + | − |
| E10-17 | + | + | " | " | " | + | + | + | + | + | + | − |
| E10-19 | + | + | " | " | " | + | + | + | + | + | + | − |
| E6-20 | + | + | " | " | " | + | + | + | + | + | + | − |
| E6-22 | + | + | " | " | " | + | + | + | + | + | + | − |
| E2-1 | + | + | " | " | " | + | + | + | + | + | + | − |
| E8-10 | + | + | " | " | " | + | + | + | + | + | + | − |
| E7-34 | + | + | " | " | " | + | + | + | + | + | + | − |
| E8-62 | + | + | " | " | " | + | + | + | + | + | + | − |
| E8-64-22 | + | + | " | " | " | + | + | + | + | + | + | − |
| E10-3 | + | + | " | " | " | + | + | + | + | + | + | − |
| E10-5 | + | + | " | " | " | + | + | + | + | + | + | − |
| E10-6 | + | + | " | " | " | + | + | + | + | + | + | − |
| E10-8 | + | + | " | " | " | + | + | + | + | + | + | − |
| E10-15 | + | + | " | " | " | + | + | + | + | + | + | − |
| E10-12 | + | + | " | " | " | + | + | + | + | + | + | − |
| E10-11 | + | + | " | " | " | + | + | + | + | + | + | − |
| E10-14 | + | + | " | " | " | + | + | + | + | + | + | − |
| E6-18 | + | + | " | " | " | + | + | + | + | + | + | − |

The process of our invention in one aspect is applicable to any *Pichia pastoris* alcohol-assimilating strain thereof. This is considered important, since not all *Pichia pastoris* strains assimilate a lower alcohol. Those which are so characterized, however, are considered by us as suitable initiating strains of *Pichia pastoris* to produce other strains of mutants of high methionine producing capabilities.

EXAMPLES

In all of the following examples, the media used are chosen from one of the following compositions:

| Medium Code | Composition[a] | |
|---|---|---|
| IM1 | KH$_2$PO$_4$ | 5.0 g |
| | CaCl$_2$.2H$_2$O | 0.1 g |
| | MgSO$_4$.7H$_2$O | 0.5 g |
| | KCl | 0.5 g |
| | (NH$_4$)$_2$SO$_4$ | 3.0 g |
| | TM[b] | 2.5 mL |
| | H$_2$O | 1.0 L |
| IM1M | IM1 + 0.5 vol.% MeOH | |
| IM1G | IM1 + 5 g Glucose | |
| IM1GE | IM1G + 3 g/L Ethionine | |
| IM1GNL | IM1G + 3 g/L Norleucine | |
| IM2 | KH$_2$PO$_4$ | 2.0 g |
| | K$_2$HPO$_4$ | 3.0 g |
| | MgSO$_4$.7H$_2$O | 0.4 g |
| | CaCl$_2$.2H$_2$O | 0.04 g |
| | NaCl | 0.1 g |
| | (NH$_4$)$_2$SO$_4$ | 2.0 g |
| | TM[b] | 1.0 mL |
| | H$_2$O | 1.0 L |

-continued

| Medium Code | Composition[a] |
|---|---|
| IM2G | IM2 + 5 g Glucose |

[a] All media contain 4 × 10$^{-6}$ g/L of biotin
[b] TM, trace minerals, CuSO$_4$.5H$_2$O, 60 mg; KI, 80 mg; MnSO$_4$.H$_2$O, 300 mg; Na$_2$MoO$_4$.2H$_2$O, 200 mg; H$_3$BO$_3$, 20 mg; ZnSO$_4$.7H$_2$O, 2 g; FeCl$_3$.6H$_2$O, 4.8 g; H$_2$O, 1L; H$_2$SO$_4$, 3 mL.

Continuous culture of yeast cells has been previously described in copending application Ser. No. 110,457 filed Jan. 15, 1980, now abandoned and refiled as continuation-in-part Ser. No. 316,164 filed Oct. 29, 1981, now U.S. Pat. No. 4,414,329.

Methionine content of the novel yeasts of this invention were analyzed by the method of MacKenzie and Tenaschuk (J. Chromatograph 97, 19–24, 1974).

Spontaneous Mutation

Exponentially growing yeast cells were spread onto IM2G plates containing an antimetabolite (relative to methionine). The antimetabolite chosen in our work was ethionine. The plates were incubated at 30° C. for several days. The colonies resistant to ethionine were then picked. The analog of methionine present in the medium turns off the synthesis of methionine in the cells. Of course, the analog cannot be incorporated into the protein. This method of treatment then produces a selection of those colonies resistant to ethionine, and, in turn, of enhanced methionine production.

Mutagenesis

Alternatively, the yeast cells were exposed to a mutagen. Mutagens can be selected from a variety of chemicals or other exposures. Desired are nonrevertable, conditional mutants to avoid possibilities of strain degeneration. For those mutants which we have developed and discovered, and deposited, no degeneration has been observed, and thus these mutants are highly desirable for industrial uses.

The mutagen or mutagenic agent selected should be one powerful enough to effect production of nonrevertable mutations. In some cases a weak mutagen can be combined with a strong mutagen. Among the weak mutagens are 2-aminopurine, 5-bromouracil, hydroxylamine, sodium bisulfide, and others. Strong mutagens are such as ethylmethane sulfonate, nitrosoguanidine (N-methyl-N-nitro-N-nitrosoguanidine), ICR 191 (an acridine derivative; see structure given in FIG. 15A, page 130, of Miller, *Experiments in Molecular Genetics* (1972, Cold Spring Harbor Laboratory)), nitrous acid though relatively high amounts may be needed, ultraviolet radiation in significant amounts, x-ray, and others.

Presently preferred is ethylmethane sulfonate because of its ready availability, its relatively powerful mutagenic nature, and its relative ease and safety of handling.

In our conversions, the invention broadly can be applied to alcohol assimilating *Pichia pastoris* strains, and any strong mutagen can be employed, using amounts and exposure techniques as known in the art. Reference to examples contained herein further describe the particular techniques employed in developing the strains of our discovery.

EXAMPLE I

Preparation of Exponentially Growing Yeast 100 mL YM medium were inoculated with a loop full (about $0.5-10 \times 10^6$ cells) of *Pichia pastoris* NRRL Y-11430 and incubated overnight at 30° C. on a gyrotary shaker (New Brunswick Scientific, model G-25). At 8–12 hour intervals, the culture was diluted by a factor of 20–100/1, depending on the turbidity of the culture. Thus, 1–5 mL of the growing culture was diluted to 100 mL with fresh YM medium. The fourth such dilution (carried out at the end of the second day of such transfers) was made so as to obtain an absorbance at 600 nm of about 1.0 after an additional 8–12 hours incubation. The appropriate dilution necessary was determined by trial and error, but generally was about 100/1, though the actual dilution carried out may vary considerably from this value, say 10–500/1.

EXAMPLE II

Mutagenesis

To a 250 mL Erlenmeyer flask were added a 10 mL solution of exponentially growing yeast cells in IM1G media. An 0.4 mL aliquot of ethylmethane sulfonate was added to the flask, which was then shaken for 45 minutes on a gyrotary shaker (New Brunswick Scientific, model G-25) at room temperature (25° C.). This incubation resulted in greater than 98% killing of the yeast cells as determined by viable counts.

The ethylmethane sulfonate treated culture then was subjected to centrifugation at about $10,000 \times g$ for 10 minutes to separate the yeast cells from the ethylmethane sulfonate containing medium. The yeast cells were resuspended in 40 mL of IM1 medium and again subjected to centrifugation at about $10,000 \times g$ for about 10 minutes. The yeast cells so washed were suspended in 100 mL fresh IM1G medium and incubated at 30° C. for about 10 hours (1–2 generations). The cell density of surviving yeast cells was determined with a Petroff-Hausser counting chamber. Necessary dilutions were made to give 150–200 colonies per plate for subsequent spreading onto plates containing IM1GE or IM1GNL medium. These plates were incubated at 30° C. for 3 days, at which time the viable colonies were retrieved with toothpicks for further purification.

The isolated single colonies were suspended in 0.5 mL of IM2G medium. The plates were incubated at 30° C. for 2 days. A single colony was picked from the first streak plate, resuspended in 0.5 mL of IM2 medium, and again streaked on plates containing IM2G medium. Material thus purified was subjected to cross-feeding studies as described below.

EXAMPLE III

Cross-Feeding Study

Approximately 1 million cells of *B. subtilis* 1A145 (purB6 metB5 leuA6) provided by the Bacillus Genetic Stock Center at Ohio State University, Columbus, Ohio, were spread on a plate containing IM2G medium supplemented with 50 ug/mL each of adenine and leucine. The viable yeast colonies obtained from the ethionine and norleucine feeding described above were gridded onto the *B. subtilis* inoculated plates. The plates were incubated at 30° C. for 3 days, at which time those colonies surrounded by satellite growth of *B. subtilis* were collected for further testing.

EXAMPLE IV

Methionine Determination 100 mL of IM1M medium in a 250 mL Erlenmeyer flask was inoculated with yeast cells isolated from the cross-feeding studies, described above. These were maintained at room temperature until all methanol was consumed, as determined by gas chromatography. One portion of the culture was subjected to direct drying on a freeze-dryer and another portion subjected to centrifugation at about $10,000 \times g$ for 10 minutes. Both the supernatant and pellet fractions from the centrifugation were freeze-dried. All three samples were analyzed for methionine content by the method described above. The results are presented in the Table.

TABLE

| Sample | Methionine Content, wt % | | |
|---|---|---|---|
| | Freeze-Dried | Pellets | Supernatant |
| Parent (NRRL Y-11430) | 0.74 | | |
| " | 0.84 | | |
| " | 0.57 | | |
| Mutant Yeasts | | | |
| E6-18 | 2.01 | | |
| E8-5 | 2.26 | | |
| E8-10 | 2.60 | | |
| E8-17 | 2.58 | | |
| E8-31 | 2.68 | | |
| E8-62 | 2.89 | | |
| E8-64 | 3.12 | | |
| E10-5 | 2.78 | | |
| E10-6 | 2.96 | | |
| E-10-9 | 2.74 | 2.70 | 0.07 |
| " | 2.34 | 3.07 | 0.15 |
| " | 2.44 | 2.83 | 0.14 |
| E10-14 | 1.82 | | |
| E10-19 | 2.37 | | |

TABLE-continued

| Sample | Methionine Content, wt % | | |
|---|---|---|---|
| | Freeze-Dried | Pellets | Supernatant |
| E6-12 | 1.71 | | |
| E6-15 | 2.16 | | |
| E8-34 | 2.31 | 2.23 | |
| " | 2.29 | 2.45 | |
| " | 3.25 | | |
| E10-17 | 2.13 | 3.58 | 0.14 |
| " | 3.19 | 2.67 | |
| E6-20 | 1.85 | | |
| E6-22 | 2.16 | | |
| E10-7 | 2.47 | | |
| " | 3.13 | 3.05 | 0.27 |
| E8-43 | 2.46 | | |
| E8-64-22 | 2.31 | | |
| E8-64-94 | 2.50 | | |
| E10-10 | 2.47 | | |
| E10-12 | 2.44 | | |
| E2-1 | 2.27 | | |
| E8-52 | 2.36 | | |
| E8-60 | 1.47 | | |
| E10-4 | 1.33 | | |
| E10-8 | 2.48 | | |
| E10-11 | 2.42 | | |
| E4 | 0.43 | | |
| E8-50 | 2.25 | | |
| E8-64-12 | 2.17 | | |
| E8-64-45 | 2.57 | | |
| E8-64-48 | 3.21 | | |
| E8-64-48 | 3.97 | 2.94 | |

A number of mutant yeasts were obtained exhibiting greatly enhanced methionine content compared to the parent yeast. In addition, the comparative results for freeze-dried vs. centrifuged cells indicate that virtually all methionine content is incorporated in the yeast cells, and thus would not be lost in further processing steps, such as feed formulation. The high methionine yeasts of the present invention are therefore seen to provide a protein supplement high in nutritionally available methionine.

Fermentation Process For The Production of Single Cell Protein

In accordance with the one aspect of our invention, single-cell protein products of increased methionine content are produced from aerobic fermentation culture procedures utilizing any of the strains we have developed, employing aerobic aqueous fermentation, preferably continuous, on a suitable carbon energy substrate of an oxygenated hydrocarbon nature, particularly a lower alcohol, preferably methanol or ethanol, most preferably methanol, employing nutrient mineral salts, assimiable nitrogen source, oxygen, added vitamins as necessary such as biotin and/or thiamine.

Fermentation Conditions

Any of the standard fermentation conditions for aerobic fermentation on an oxygenated hydrocarbon feedstock can be employed, the presently preferred conditions are those where high concentrations are maintained in the ferment. It is necessary to supply suitable amounts in proper proportions of selected mineral nutrients in the feed media, in order to assure proper microorganism growth, to maximize assimilation of the carbon and energy source by the cells in the microbial conversion process, and to achieve maximum cellular yields with maximum cell density in the fermentation media.

Although the composition of the ferment can vary over a wide range, depending in part on the yeast and substrate employed, the minerals content in the ferment (that is, liquid plus cells) in accordance with our invention is relatively high, at higher levels than heretofore considered suitable or practical by the prior art. Set forth in the table below are the minimum, broad, and presently preferred ranges of concentrations of various elements in the ferment, the concentration being expressed as of the element, though it is recognized that all or part of each can be present in the form of a soluble ion, or in cases such as P are present in a combined form of some type such as phosphate. The amount of each element is expressed in grams or milligrams per liter of ferment (aqueous phase, including cells):

| | Weight of Element per Liter of Ferment | | |
|---|---|---|---|
| Element | Minimum | Broad Range | Preferred Range |
| P | 1.9 g | 1.9–20 g | 2.2–10 g |
| K | 1 g | 1–20 g | 1.5–10 g |
| Mg | 0.15 g | 0.15–3 g | 0.3–1.2 g |
| Ca | 0.06 g | 0.06–1.6 g | 0.08–0.8 g |
| S | 0.1 g | 0.1–8 g | 0.2–5 g |
| Fe | 6 mg | 6–140 mg | 9–80 mg |
| Zn | 2 mg | 2–100 mg | 3–40 mg |
| Cu | 0.6 mg | 0.6–16 mg | 1–10 mg |
| Mn | 0.6 mg | 0.6–20 mg | 0.9–8 mg |

Sulfur desirably is employed in the form of a sulfate. Some of the metals required are advantageously added in the form of a sulfate, so that the minimum concentrations of sulfur normally are exceeded. Any or all of the metals listed can be used or present as the sulfate. Preferably, the magnesium, calcium, iron, zinc, copper, and manganese are employed in the form of a sulfate or chloride, or in the form of a compound which is converted in situ to a sulfate or chloride. The potassium preferably is employed as a sulfate, chloride, or phosphate or in the form of a compound which is converted in situ to a sulfate, chloride, or phosphate. The phosphorus preferably is employed in the form of phosphoric acid or in the form of a phosphate, monohydrogen phosphate, or dihydrogen phosphate, e.g., as a potassium or ammonium salt, or as a compound which is converted in situ to such a salt.

Other elements which may be present, at least in trace amounts, include such as sodium and cobalt, e.g., as a halide or sulfate, molybdenum, e.g., as molybdate; boron, e.g., as borate; selenium, e.g., as selenite or selenate; or iodine, e.g., as iodide.

In typical high cell density fermentation, the ferment will comprise about one-half supernatant medium and one-half cells, by volume. These one-half by volume cells, however, will contain at least about two-thirds of the mineral salts content of the ferment.

The presently preferred substrates for aqueous fermentation conditions are the carbon-oxygen-hydrogen significantly water-soluble compounds. The term "oxygenated hydrocarbon" is intended to be a generic term in this disclosure descriptive of compounds employable, and not necessarily a limiting term referring to the source of the substrate. For this disclosure, the oxygenated hydrocarbons include the water-soluble carbohydrates, as well as those alcohols, ketones, esters, acids, and aldehydes, and mixtures, which are reasonably significantly water-soluble in character generally of 1 to 20 carbon atoms per molecule.

Oxygenated hydrocarbons examples include methanol, ethanol, ethylene glycol, propylene glycol, 1-propanol, 2-propanol, glycerol, 1-butanol, 2-butanol, 3-methyl-1-butanol, 1-pentanol, 2-hexanol, 1,7-heptanediol, 1-octanol, 2-decanol, 1-hexadecanol, 1-eicosanol, acetone, 2-butanone, 4-methyl-2-pentanone, 2-decanone, 3-pentadecanone, 2-eicosanone, formaldehyde, acetaldehyde, propionaldehyde, butyraldehyde, hexanol, 7-methyloctanal, tetradecanal, eicosanal, acetic acid, propionic acid, butyric acid, glutaric acid, 5-methylhexanoic acid, acelaic acid, dodecanoic acid, eicosanoic acid, methyl formate, methyl acetate, ethyl acetate, propyl butyrate, isopropyl hexanoate, hexyl 5-methyloctanoate, octyl dodecanoate, and the like, as well as mixtures thereof.

Presently preferred are the water-soluble alcohols of 1 to 4 carbon atoms, water-soluble acids of 2 to 4 carbon atoms, and the water-soluble carbohydrates. Preferred are the water-soluble monohydric aliphatic hydrocarbyl alcohols. It should be noted that 2-methyl-1-propanol is inhibitory to some yeasts, and in fermentations with such yeasts this alcohol should be avoided. Presently most preferred are the alcohols of 1 to 4 carbon atoms (other than 2-methyl-1-propanol); of these, methanol and ethanol presently are preferred over the others; and methanol is the most preferred, due to the low relative cost of such feedstock.

Petroleum gases can be oxidized, and the water-soluble materials employed, such as oxidation of methane, ethane, and the like, to provide mixtures predominantly of the corresponding alcohol as well as various aldehydes, ketones, acids, and the like, and similarly suitable hydrocarbon fractions from various petroleum refinery sources produced within the integrated refining and chemical processing complex, sometimes termed a petrocomplex, can be utilized for fermentation purposes.

The salts in the supernatant are at a relatively low concentration, since there is a high take-up by the growing reproducing cells. The mineral salts in the cells may not be as fed or applied since some may be a bound organic form. Mineral analysis of the ferment, of course, would reflect a total mineral content.

In addition to the mineral salts, vitamins (organic growth factors) can be employed in the ferment as is known in the art, when their presence is desirable for the propagation of the particular yeast chosen.

The fermentation itself is an aerobic process requiring molecular oxygen which is supplied by a molecular oxygen-containing gas such as air, oxygen-enriched air, or even substantially pure molecular oxygen, to maintain the ferment with an oxygen partial pressure effective to assist the microorganism species in growing in a thriving fashion. By using an oxygenated hydrocarbon substrate, the total oxygen requirements for growth of the microorganism are reduced from the requirements when a paraffin is used. Even so, adequate quantities of molecular oxygen must be supplied for growth, since the assimilation of the substrate and corresponding growth of the microorganisms is, in part, a combustion process.

The rate at which molecular oxygen is supplied to the ferment should be such that the growth of the yeast is not limited by lack of oxygen. Fermentor designs vary widely in their ability to transfer oxygen to the culture. Although the overall aeration rates can vary over a considerable range, with fermentors that are very efficient in oxygen transfer aeration generally is conducted at a rate of about 0.5 to 8, preferably about 1 to 6, volumes (at the pressure employed and at 25° C.) of molecular oxygen-containing gas per liquid volume in the fermentor per minute. This amount is based on air of normal oxygen content being supplied to the reactor, and in terms of pure molecular oxygen the respective ranges would be about 0.1 to 1.7, or preferably about 0.2 to 1.3, volumes (at the pressure employed and at 25° C.) of molecular oxygen per liquid volume in the fermentor per minute.

The pressure employed for the microbial fermentation step can range widely. Typical pressures are about 0 to 150 psig, presently preferably about 0 to 60 psig, more preferably at least slightly over atmospheric pressure, as a balance of equipment and operating costs versus oxygen solubility is achieved. Greater than atmospheric pressures are advantageous in that such pressures do tend to increase the dissolved oxygen concentration in the aqueous ferment, which in turn can help increase cellular growth rates. At the same time this is counterbalanced by the fact that high pressures do increase equipment and operating costs.

The fermentation temperatures can vary somewhat, but generally should be in the range of about 25° C. to 65° C., preferably about 28° C. to about 50° C., though preferably for these strains, close to about 30° C.

Yeasts require a source of assimilable nitrogen. The assimilable nitrogen can be supplied by any nitrogen-containing compound or compounds capable of releasing nitrogen in a form suitable for metabolic utilization by the yeast microorganism. While a variety of organic nitrogen source compounds, such as protein hydrolysates, technically can be employed, usually cheaper nitrogen-containing compounds such as ammonia, ammonium hydroxide, urea, and various ammonium salts such as ammonium phosphate, ammonium sulfate, ammonium pyrophosphate, and ammonium chloride can be utilized. Ammonia gas itself is convenient for large scale operations, and can be employed by bubbling through the aqueous microbial ferment in suitable amounts. At the same time, such ammonia also assists in pH control.

The pH range in the aqueous microbial ferment should be in the range of about 3 to 7, more preferably and usually about 3.5 to 5.5. Preferences of certain microorganisms for a pH range are dependent to some extent on the medium employed, as well as on the particular microorganism, and thus may change somewhat with change in medium as can be readily determined by those skilled in the art.

The average retention time of the ferment in the fermentor can vary considerably, depending in part on the fermentation temperature and yeast culture employed. Generally, the retention time will be about 2 to 30 hours, preferably presently about 4 to 14 hours, based on average retention.

High concentrations of some of the described carbon and energy substrates, particularly such as methanol or formaldehyde or the like, may be inhibitory to satisfactory microbial growth or even toxic to the microorganisms in the fermentation. Relatively high concentrations of substrates thus should be avoided, so that it is generally desirable to maintain the substrate concentration in the ferment at a maximum tolerable level. With some of the lower alcohols, this level in the ferment generally is about 0.001 to 5 volume percent, preferably about 0.01 to 0.05 volume percent, while with the aldehydes the level should be one-tenth of these due to the toxicity of aldehydes, so as to neither starve nor inhibit the growth rates of the microorganism chosen.

When the carbon and energy source material contains an aldehyde in amounts potentially deleterious to the microorganism, the deleterious aldehyde effects can be alleviated by first treating the substrate with a suitable amount of a nitrogen-containing compound, preferably ammonia, ammonium hydroxide, or other active ammonium compound, in a ratio of about 0.01 to 10 mol equivalents of such nitrogen-containing compounds per mol of aldehyde. Such a treated substrate then is not only the carbon energy source, but also contains at least a portion of the necessary assimilable nitrogen.

Conveniently, the fermentation is conducted in such a manner that the carbon-containing substrate can be controlled as a limiting factor, thereby providing good conversion of the carbon-containing substrate to yeast cells and avoiding potential contamination of the yeast cells with a substantial amount of unconverted substrate. The latter is not a problem with water-soluble substrates, since any remaining traces are readily washed off. It may be a problem, however, in the case of non-water-soluble substrates such as the higher n-paraffins, requiring added product treatment steps such as removal of residual hydrocarbon by suitable solvent washing steps.

Continuous operation is much to be preferred for ease of control in production of uniform quantities of uniform products, and most economical uses of all equipment. In a continuous process, the carbon and energy source material as substrate, aqueous mineral medium, assimilable nitrogen source, and molecular oxygen-containing gases, are added continuously to the ferment in the fermentor combined with continuous withdrawal of ferment. Although the volume ratio of added carbon energy substrate:added aqueous mineral medium can vary over a wide range, depending in part on the nature of the carbon-containing substrate, generally it will be in the range of about 1:9 to 6:4, presently and preferably in the range of about 2:8 to 5:5.

If desired, part or all of the carbon energy source material and/or part of the assimilable nitrogen source such as ammonia can be added to the aqueous mineral medium prior to passing the aqueous mineral medium to the fermentor. Most convenient in our work in high-cell density fermentations has been the use of a feed ratio of about 40 volume percent alcohol to 60 volume percent mineral salts medium.

Each of the streams introduced into the reactor preferably is controlled at a predetermined rate, or in response to a need determinable by monitoring, such as concentration of the carbon and energy substrate, pH, dissolved oxygen, oxygen or carbon dioxide in the off-gases from the fermentor, cell density measurable by light transmittancy, or the like. The feed rates of the various materials can be varied so as to obtain as rapid a cell growth rate as possible, consistent with efficient utilization of the carbon and energy source, to obtain as high a yield of yeast cells relative to substrate charge as possible. Thus, by the process of our invention, yeast cells can be obtained in yields of about 30 to 110 grams per 100 grams substrate charged, depending in part on the particular substrate used.

All equipment, reactor, or fermentation means, vessel or container, piping, attendant circulating or cooling devices, and the like, most preferably are sterilized, usually by employing steam such as at about 250° F. (121° C.) for at least about 15 minutes. The sterilized reactor is inoculated with a culture of the specified microorganism in the presence of all the required nutrients, including molecular oxygen, and the carbon-containing substrate.

The type of fermentor employed is not critical in the practice of the fermentation process of our invention, though presently preferred is operation in a foam-filled fermentor. A fermentor designed to encourage and maintain the produced foam is beneficial to the process of achieving the increased oxygen transfer necessary to maintain desired high cell densities and rapid growth rates.

In starting out a fermentation, the aqueous mineral medium, suitable concentration of carbon source, assimilable nitrogen, trace components where desired, and the starting innoculum of yeast are placed in a sterilized fermentor, and suitable flows of oxygen and the various feeds are gradually commenced. If desired, the initial fermentation substrate can be such as glucose, with gradual change to such as methanol as cell density builds up. It is possible to begin at low mineral salts levels in the aqueous ferment and build up to a high mineral salts level by feeding an aqueous mineral medium having a high concentration of mineral salts to the ferment, though we normally simply add high salts medium initially to the fermentor to commence immediate operation. One skilled in the art realizes that a brief lag time will usually occur at start up before the inoculum builds up enough cells for full input of salts and substrate to be utilized.

Product Recovery

The yeast cells produced in the high cell density process can be recovered. If desired, extracellular products can be recovered from the substantially cell-free remaining supernatant liquid by conventional means. The substantially cell-free effluent can be treated, for example, with acetone or a lower alcohol such as methanol or ethanol to precipitate any polymeric material produced extra-cellularly. The cell-free effluent also can be treated by solvent extraction and/or base extraction to recover, if desired, other extra-cellular products such as pigments, vitamins, or organic acids produced during the culturing process. The cell-free effluent, with or without such intervening treatment, can be returned to the fermentor as a part of the aqueous makeup, or as a substantial or almost total part of the aqueous makeup, to avoid waste disposal problems insofar as possible.

The microbial cells usually are killed by heat or chemical means, and this can be done before or after the separation of the cells from the fermentor effluent. The yeast cells are a valuable source of protein for man as well as beast. For human consumption, the cells can be treated as necessary to reduce the nucleic acid, but for animal feed purposes such treatment does not appear presently necessary.

In a process employing high cell density operation, e.g., a cell density within the range of about 60 to 160, preferably about 70 to 150, grams of yeast cells, on a dried basis, per liter of fermentation admixture, can be obtained in high yield. If desired, the cells can be recovered from the fermentation admixture by centrifugation or other separation means. Also, if desired, the concentrated cells then can be washed such as by mixing with water, and separated such as by recentrifuging, or by adding water prior to or during centrifugation to substantially free the cells of mineral medium, and the washings including the separated mineral medium then can be returned to the fermentor as water and mineral medium makeup, thus substantially reducing or avoiding waste disposal problems. The recovered cells then can be simply dried to produce a dried product for future use. If desired, the high cell density fermentor effluent in total can be dried to produce a whole dried product of dried cells and residual water soluble substances including salts, and this whole-dried product used as a very useful animal feed of high protein-high salts character.

The disclosure, including data, illustrates the value and effectiveness of our invention. The examples, the knowledge and background of the field of the invention, general principles of microbiology, chemistry, and other applicable sciences, have formed the bases from which the broad descriptions of our invention, including the ranges of conditions and generic groups of operant components, have been developed, and which have formed the bases for our claims here appended.

We claim:

1. A method of producing a single cell protein material which comprises culturing under aerobic aqueous fermentation conditions at least one high methionine producing *Pichia pastoris* species in aqueous ferment employing effective amounts of oxygenated hydrocarbon energy substrate, assimilable nitrogen source, and mineral salts medium, and recovering the resulting cellular products as a single cell protein material, wherein said high methionine producing *Pichia pastoris* species is selected from the group consisting of:
   *Pichia pastoris* Y-12439,
   *Pichia pastoris* Y-12440,
   *Pichia pastoris* Y-12441,
   *Pichia pastoris* Y-12442,
   *Pichia pastoris* Y-12443,
   *Pichia pastoris* Y-12444,
   *Pichia pastoris* Y-12445,
   *Pichia pastoris* Y-12446,
   *Pichia pastoris* Y-12448,
   *Pichia pastoris* Y-12449,
   *Pichia pastoris* Y-12450,
   *Pichia pastoris* Y-12451,
   *Pichia pastoris* Y-12452,
   *Pichia pastoris* Y-12453,
   *Pichia pastoris* Y-12454,
   *Pichia pastoris* Y-12455,
   *Pichia pastoris* Y-12456,
   *Pichia pastoris* Y-12458,
   *Pichia pastoris* Y-12459,
   *Pichia pastoris* Y-12460,
   *Pichia pastoris* Y-12461,
   *Pichia pastoris* Y-12462,
   *Pichia pastoris* Y-12463,
   *Pichia pastoris* Y-12465,
   *Pichia pastoris* Y-12466,
   *Pichia pastoris* Y-12467,
   *Pichia pastoris* Y-12469,
   *Pichia pastoris* Y-12470, and
   *Pichia pastoris* Y-12493.

2. The process according to claim 1 wherein said carbon energy source is selected from the group consisting of alcohols, ketones, aldehydes, organic acids, esters, and mixtures thereof.

3. The process according to claim 2 wherein said oxygenated hydrocarbon is selected from the group consisting of methanol, ethanol, ethylene glycol, propylene glycol, 1-propanol, 2-propanol, glycerol, 1-butanol, 2-butanol, 3-methyl-1-butanol, 1-pentanol, 2-hexanol, 1,7-heptanediol, 1-octanol, 2-decanol, 1-hexadecanol, 1-eicosanol, acetone, 2-butanone, 4-methyl-2-pentanone, 2-decanone, 3-pentadecanone, 2-eicosanone, formaldehyde, acetaldehyde, propionaldehyde, butyraldehyde, hexanal, 7-methyloctanal, tetradecanal, eicosanal, acetic acid, propionic acid, butyric acid, glutaric acid, 5-methylhexanoic acid, azelaic acid, dodecanoic acid, eicosanoic acid, methyl formate, methyl acetate, ethyl acetate, propyl butyrate, isopropyl hexanoate, hexyl 5-methyloctanoate, octyl dodecanoate, and mixtures thereof.

4. The process according to claim 2 wherein said carbon energy source material is an alcohol of 1 to 4 carbon atoms.

5. The process according to claim 4 wherein said alcohol is methanol or ethanol.

6. The process according to claim 5 employing aqueous fermentation conditions of temperature in the range of 25° C. to 65° C., pH in the range of about 3 to 7, pressure in the range of about 0 to 150 psig, and a fermentation time in the range of about 2 to 30 hours based on average retention.

7. The process according to claim 5 wherein said alcohol is methanol.

8. A biologically pure culture of yeast of a *Pichia pastoris* selected from the group consisting of:
   *Pichia pastoris* Y-12439,
   *Pichia pastoris* Y-12440,
   *Pichia pastoris* Y-12441,
   *Pichia pastoris* Y-12442,
   *Pichia pastoris* Y-12443,
   *Pichia pastoris* Y-12444,
   *Pichia pastoris* Y-12445,
   *Pichia pastoris* Y-12446,
   *Pichia pastoris* Y-12448,
   *Pichia pastoris* Y-12449,
   *Pichia pastoris* Y-12450,
   *Pichia pastoris* Y-12451,
   *Pichia pastoris* Y-12452,
   *Pichia pastoris* Y-12453,
   *Pichia pastoris* Y-12454,
   *Pichia pastoris* Y-12455,
   *Pichia pastoris* Y-12456,
   *Pichia pastoris* Y-12458,
   *Pichia pastoris* Y-12459,
   *Pichia pastoris* Y-12460,
   *Pichia pastoris* Y-12461,
   *Pichia pastoris* Y-12462,
   *Pichia pastoris* Y-12463,
   *Pichia pastoris* Y-12465,
   *Pichia pastoris* Y-12466,
   *Pichia pastoris* Y-12467,
   *Pichia pastoris* Y-12469,
   *Pichia pastoris* Y-12470, and
   *Pichia pastoris* Y-12493,
said culture being capable of producing recoverable amounts of single-cell protein upon aerobic fermentation in an aqueous nutrient medium containing assimilable amounts of carbon, nitrogen, organic growth factors, and inorganic nutrients, wherein said carbon is substantially supplied in the form of an oxygenated hydrocarbon compound.

9. A biologically pure culture according to claim 8 wherein said yeast is *Pichia pastoris* E6-15 NRRL Y-12439.

10. A biologically pure culture according to claim 8 wherein said yeast is *Pichia pastoris* E6-18 NRRL Y-12440.

11. A biologically pure culture according to claim 8 wherein said yeast is *Pichia pastoris* E8-5 NRRL Y-12441.

12. A biologically pure culture according to claim 8 wherein said yeast is *Pichia pastoris* E8-17 NRRL Y-12442.

13. A biologically pure culture according to claim 8 wherein said yeast is *Pichia pastoris* E8-31 NRRL Y-12443.

14. A biologically pure culture according to claim 8 wherein said yeast is *Pichia pastoris* E8-43 NRRL Y-12444.

15. A biologically pure culture according to claim 8 wherein said yeast is *Pichia pastoris* E8-50 NRRL Y-12445.

16. A biologically pure culture according to claim 8 wherein said yeast is *Pichia pastoris* E8-52 NRRL Y-12446.

17. A biologically pure culture according to claim 8 wherein said yeast is *Pichia pastoris* E8-64 NRRL Y-12448.

18. A biologically pure culture according to claim 8 wherein said yeast is *Pichia pastoris* E8-64-12 NRRL Y-12449.

19. A biologically pure culture according to claim 8 wherein said yeast is *Pichia pastoris* E8-64-45 NRRL Y-12450.

20. A biologically pure culture according to claim 8 wherein said yeast is *Pichia pastoris* E8-64-48 NRRL Y-12451.

21. A biologically pure culture according to claim 8 wherein said yeast is *Pichia pastoris* E8-64-94 NRRL Y-12493.

22. A biologically pure culture according to claim 8 wherein said yeast is *Pichia pastoris* E10-7 NRRL Y-12452.

23. A biologically pure culture according to claim 8 wherein said yeast is *Pichia pastoris* E10-9 NRRL Y-12453.

24. A biologically pure culture according to claim 8 wherein said yeast is *Pichia pastoris* E10-10 NRRL Y-12454.

25. A biologically pure culture according to claim 8 wherein said yeast is *Pichia pastoris* E10-17 NRRL Y-12455.

26. A biologically pure culture according to claim 8 wherein said yeast is *Pichia pastoris* E10-19 NRRL Y-12456.

27. A biologically pure culture according to claim 8 wherein said yeast is *Pichia pastoris* E6-22 NRRL Y-12458.

28. A biologically pure culture according to claim 8 wherein said yeast is *Pichia pastoris* E2-1 NRRL Y-12459.

29. A biologically pure culture according to claim 8 wherein said yeast is *Pichia pastoris* E8-10 NRRL Y-12460.

30. A biologically pure culture according to claim 8 wherein said yeast is *Pichia pastoris* E8-34 NRRL Y-12461.

31. A biologically pure culture according to claim 8 wherein said yeast is *Pichia pastoris* E8-62 NRRL Y-12462.

32. A biologically pure culture according to claim 8 wherein said yeast is *Pichia pastoris* E8-64-22 NRRL Y-12463.

33. A biologically pure culture according to claim 8 wherein said yeast is *Pichia pastoris* E10-5 NRRL Y-12465.

34. A biologically pure culture according to claim 8 wherein said yeast is *Pichia pastoris* E10-6 NRRL Y-12466.

35. A biologically pure culture according to claim 8 wherein said yeast is *Pichia pastoris* E10-8 NRRL Y-12467.

36. A biologically pure culture according to claim 8 wherein said yeast is *Pichia pastoris* E10-12 NRRL Y-12469.

37. A biologically pure culture according to claim 8 wherein said yeast is *Pichia pastoris* E10-11 NRRL Y-12470.

* * * * *